United States Patent
Kaji et al.

(10) Patent No.: US 7,357,795 B2
(45) Date of Patent: Apr. 15, 2008

(54) MEDICAL DEVICE AND METHOD OF EMBOLIZING BRONCHUS OR BRONCHIOLE

(75) Inventors: Hinako Kaji, Hachiouji (JP); Kunihide Kaji, Hachiouji (JP)

(73) Assignee: Olympus Corporation, Tokyo (JP)

( * ) Notice: Subject to any disclaimer, the term of this patent is extended or adjusted under 35 U.S.C. 154(b) by 654 days.

(21) Appl. No.: 10/198,779

(22) Filed: Jul. 19, 2002

(65) Prior Publication Data

US 2003/0018344 A1 Jan. 23, 2003

(30) Foreign Application Priority Data

Jul. 19, 2001 (JP) ............................. 2001-220004

(51) Int. Cl.
*A61M 31/00* (2006.01)
*A61M 29/00* (2006.01)

(52) U.S. Cl. ...................................... 604/514; 606/191

(58) Field of Classification Search ........ 604/514–516; 606/200, 108, 191; 128/898
See application file for complete search history.

(56) References Cited

U.S. PATENT DOCUMENTS

| 5,670,488 A | * | 9/1997 | Gregory et al. ................ 514/44 |
| 6,287,290 B1 | * | 9/2001 | Perkins et al. .............. 604/516 |
| 6,770,745 B2 | * | 8/2004 | Burkly et al. .......... 530/388.22 |

FOREIGN PATENT DOCUMENTS

WO WO 98/48706 11/1998

* cited by examiner

*Primary Examiner*—Vy Q. Bui
(74) *Attorney, Agent, or Firm*—Scully, Scott, Murphy & Presser, P.C.

(57) ABSTRACT

To provide a medical device and a method both of which can suitably embolize a bronchus in a target part by embolizing the bronchus with (at least a part of) a living tissue during surgical treatment of lung emphysema. For example, an injection material is injected into a submucosa by the use of a syringe, and in the injected part, a swelling swollen into the internal cavity of the bronchus is formed to tightly seal the living tissue of the bronchus or a bronchiole, thereby embolizing a target bronchus.

9 Claims, 12 Drawing Sheets

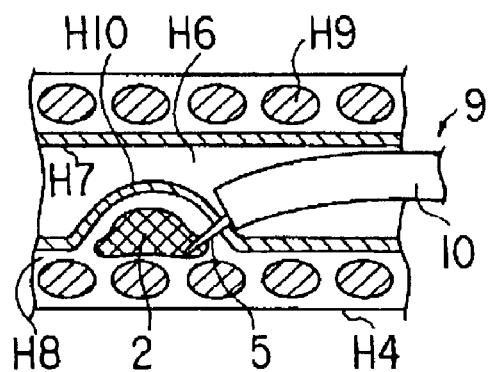
FIG. 3A
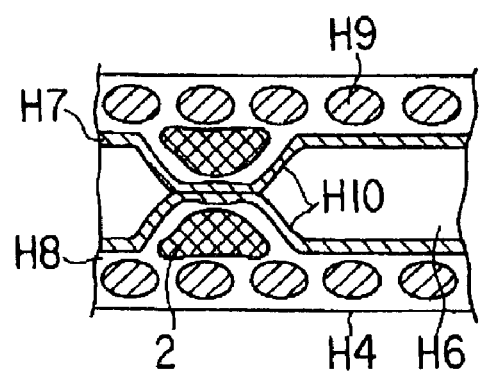
FIG. 3B
FIG. 4
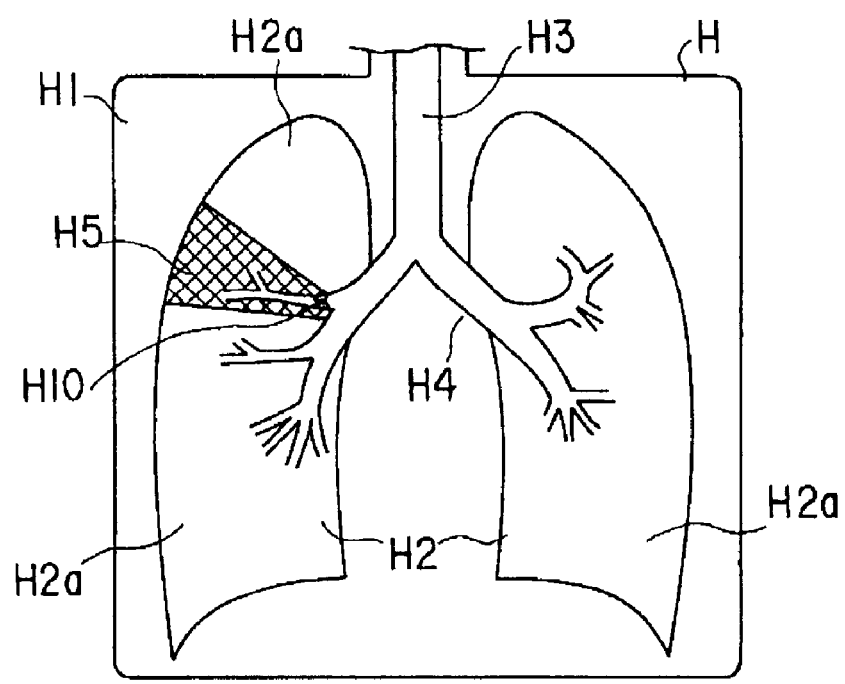

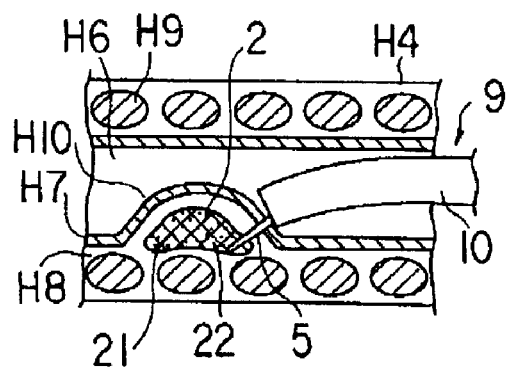
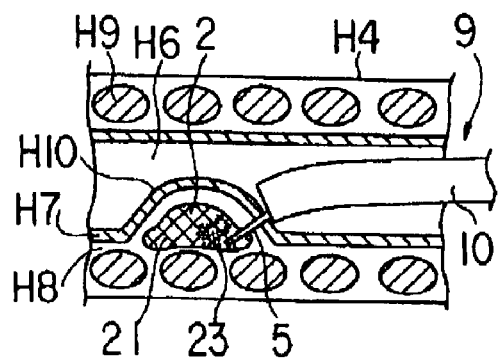
FIG. 5A          FIG. 5B
FIG. 6
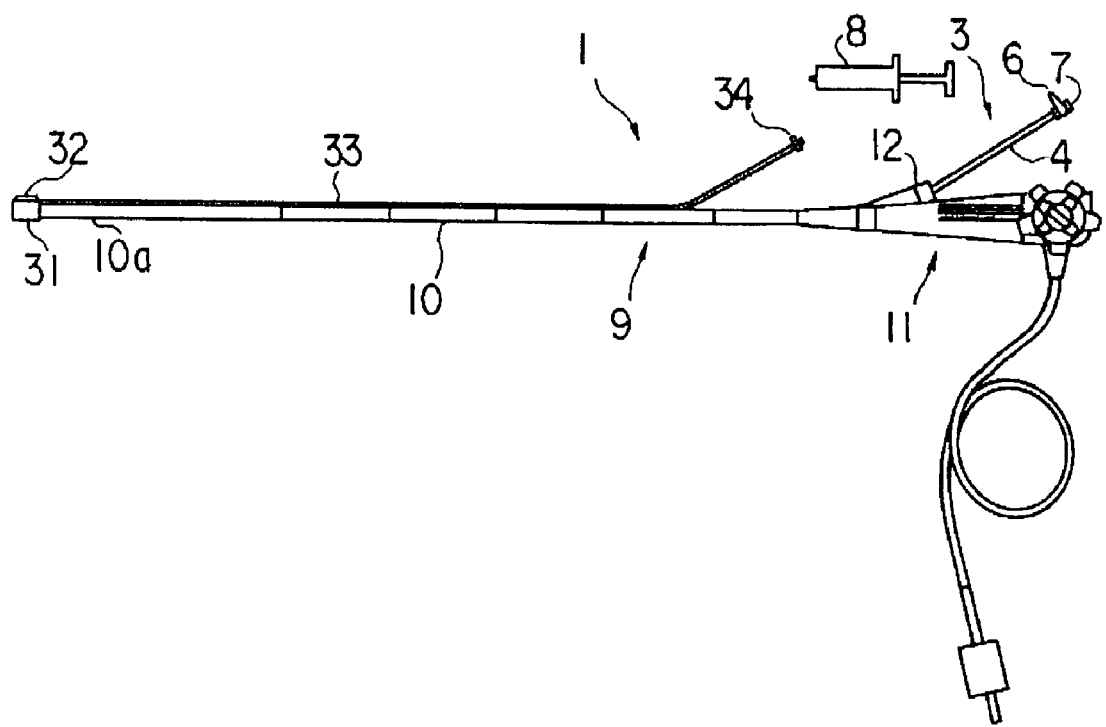

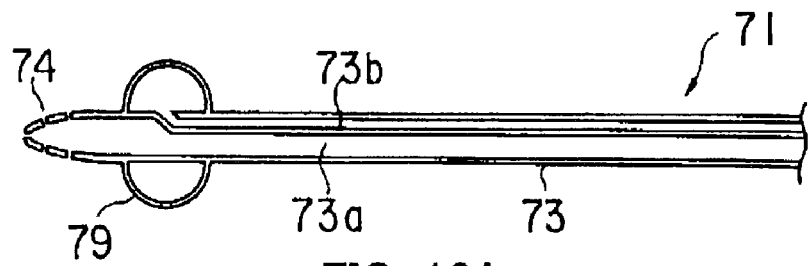
FIG. 16A
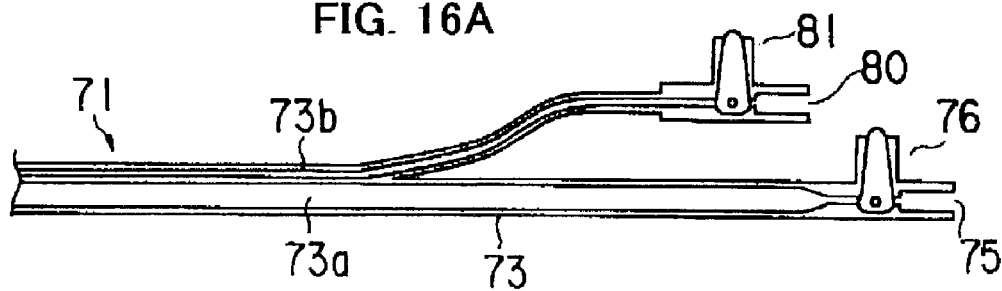
FIG. 16B
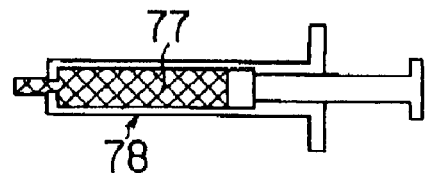
FIG. 16C
FIG. 17
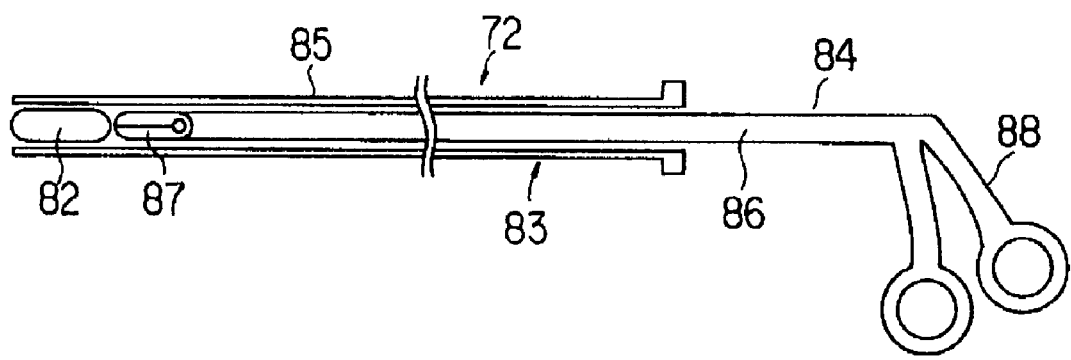

MEDICAL DEVICE AND METHOD OF EMBOLIZING BRONCHUS OR BRONCHIOLE

CROSS-REFERENCE TO RELATED APPLICATION

This application is based upon and claims the benefit of priority from the prior Japanese Patent Application No. 2001-220004, filed Jul. 19, 2001, the entire contents of the application are incorporated herein by reference.

BACKGROUND OF THE INVENTION

1. Field of the Invention

The invention relates to a method and a medical device both of which are used for embolizing a bronchus or a bronchiole, for example, during treatment of lung emphysema.

2. Description of the Related Art

In general, lung emphysema is a morbid change, which is mainly formed by inhalation of harmful substances due to smoking or the like and mainly features wide destruction in peripheral airways and alveoli. The formation of such morbid change is chronic and progressive, and the respiratory function of a patient whose lung emphysema is in an advanced stage is disordered to a remarkable extent. Respiratory disorder due to lung emphysema entails, as its basic elements of disfunction, a reduction in resiliency due to destruction of alveoli and a decrease in the area of a functional alveolar membrane, and is caused by a reduction in ventilation efficiency and a decrease in potential ability of breathing due to a combination of a plurality of elements of disfunction.

The lung tissue of a part affected by lung emphysema suffers overexpansion, and cannot achieve sufficient deflation accompanied by expiration. As the volume occupied by the affected part in a pleural cavity becomes larger, a diaphragm and a chest shift to their inflated positions and the driving force of respiratory movement decreases. The remaining normal lung tissue becomes unable to inflate sufficiently in the pleural cavity, and lowers in ventilation efficiency to a remarkable extent.

Primary methods for treatment of lung emphysema is to give a patient bronchodilators, anti-inflammatory agents and antibiotics for treatment of infectious diseases which may occur as complications, and to apply oxygen inhalation to a patient if the patient's affected part is in an advanced stage. Although there may be some cases where the symptoms of the patient are relieved by such internal medicine treatment, the advance of the patient's morbid state cannot be stopped.

On the other hand, as surgical treatment can be given to a lung emphysema patient, such as lung volume reduction surgery and lung transplantation. The lung volume reduction surgery surgically removes a part affected by emphysema to recover the remaining normal pulmonary function. In this manner, it is possible to improve the quality of life of the patient, but it is generally necessary to remove a portion as large as about 30% of the lung of the patient. Since this removal imposes a large burden on the patient, it takes a long time for the patient to recover after the surgical operation.

In the case where lung-emphysema-affected parts and normal lung tissues exist in disorder, it is difficult to separate only morbid tissues, so that there is a case in which even normal lung tissues must be removed. In addition, there is also a case where the shape of a serosa, which contains a pulmonary external surface varies, hinders the inflation of the remaining portion of the lung. As a result, there is a case where the function of the remaining normal lung tissue of the patient cannot be fully retained. In addition, since the line of a removed part differs from a natural state and is exposed to nonuniform pressure, there is a case where the tissue of the removed part is broken and pneumothorax occurs. Since lung emphysema is a progressive disease, the remaining portion of the lung of the patient is affected before long. However, the removal of lung tissue imposes a large burden on the body of the patient and, therefore, is difficult to practice repeatedly.

On the other hand, lung transplantation is the only method that can completely cure lung emphysema by replacing a lung of a patient with a normal lung. However, lung transplantation imposes a very large burden on the body of the patient, and entails problems peculiar to transplantation treatment such as immunological problems and the necessity of securing donors. Neither lung volume reduction surgery nor lung transplantation can be easily practiced, because of the problem of requiring a large surgical operation and hence a huge cost for treatment.

Lung volume reduction surgery and lung transplantation, which are practiced as surgical treatment of lung emphysema, have the following problems:

(1) Since lung volume reduction surgery and lung transplantation need a large surgical operation, a large scar is left on the body of a patient.
(2) Neither lung volume reduction surgery nor lung transplantation can be repeatedly practiced on the same patient.
(3) Lung volume reduction surgery cannot be practiced, if an affected part does not exist at a position where it can be easily removed.
(4) There is a case where lung volume reduction surgery cannot fully ensure the function of the remaining portion of the lung.
(5) Both lung volume reduction surgery and lung transplantation require huge costs.
(6) Pneumothorax may occur after a surgical operation.
(7) There are large obstacles to be surmounted, such as the necessity of securing donors and a rejection of a transplanted piece.

On the other hand, in PCT WO98/48706, an embolization element which gives treatment to lung emphysema by-embolizing a bronchus distributed in a lung-emphysema-affected part is described as a device for solving the above-described problems of surgical treatment of lung emphysema. This embolization element has a construction in which a locking element to be locked by being hooked on a living tissue is provided on a peripheral portion of the body of the embolization element. When the embolization element is to be placed in the body, the locking element provided on the periphery of the body of the embolization element is locked by being hooked on the living tissue, so that the embolization element is placed at a desired position in the body.

The embolization element of PCT WO98/48706 has a construction in which a complicated locking element is provided on the peripheral portion of the body of the embolization element in order to place the embolization element at a desired position in the body. However, PCT WO98/48706 has the problem that since the embolization element for giving treatment to lung emphysema is extremely small in size, it is difficult to manufacture the embolization element having the complicated locking element.

The present invention has been made, at least in part, by noting the above-described problems, and an object of the invention is to realize embolization of a bronchus without using an embolization element having a complicated locking element.

BRIEF SUMMARY OF THE INVENTION

The invention uses living tissue itself as an embolization material for a bronchus or a bronchiole (the living tissue may be used exclusively or used together with another medical device).

A first specific example of the invention is to puncture a mucosa of a bronchus and inject an injection material into that punctured portion, thereby swelling the inside wall of the bronchus. In this case, as a representative method of practicing the first specific example, there is a method of providing a sharp needle-like puncture portion at the leading end of a tubular catheter and connecting a syringe to the other end, and injecting an injection material from the syringe. The leading end of the catheter passes through a channel of an endoscope and is positioned in a part to be embolized, and the puncture portion is made to puncture the mucosa of a bronchus. After that, when an injection material is injected into a tissue below the mucosa of a trachea from the other end of the catheter by the syringe, the inside wall of the bronchus becomes swollen. In the part to be embolized, if a plurality of swellings are formed at different positions, the bronchus or a bronchiole can be embolized far more reliably.

In this case, the injection material preferably contains fibrin adhesive and collagen. In addition, it is preferable to adopt an injection material having the property of expanding by absorbing water inside a living body. When particles are contained as solid components in the injection material, the particles have the effect of maintaining the swellings for a long time. In this case, preferred examples of the particles contain a component of high biocompatibility, such as silicone, metal particles such as titanium particles, apatite, and β-TCP. Addition of a curing agent to the injection material after the injection also has the effect of ensuring embolization and maintaining the swellings for a long time.

The above-described puncturing manipulation is facilitated by the use of a cap element to be attached to the leading end of the endoscope. The cap element has a through-hole from which the puncture portion of the catheter projects and a sheath for guiding the puncture portion of the catheter from the leading opening of the channel of the endoscope into the through-hole. In this case, it is convenient that the through-hole be provided on a side of the cap. Furthermore, in the case where a balloon is provided on the side of the cap opposite to the side in which the through-hole is provided, expansion of the balloon makes the inside wall of the bronchus and the cap adhere closely to each other, thereby improving workability.

In the above-described treatment, instead of the endoscope, a trocar may be inserted into a pleural cavity, and the injection material may be injected from the outside of the bronchus or the bronchiole by a treatment element inserted from the trocar.

A second specific example of the invention is to puncture the mucosa of a bronchus or a bronchiole with a medical device of size approximately as large as the inside diameter of the bronchus or the bronchiole, thus proliferate a living tissue in a portion exposed out of the mucosa of the bronchus, and realize embolization of the bronchus or the bronchiole with the proliferated living tissue. In this case, it is desirable that a sharp puncture portion is provided on a puncture-side end of the medical device. Furthermore, it is desirable that a claw portion for preventing the puncture portion from coming off is formed on the puncture portion.

A third specific example of the invention is to carry a knife-shaped treatment element to a part to be embolized in a bronchus or a bronchiole, dissect and peel the mucosa of the bronchus or the bronchiole in the part to embolized with the treatment element, and embolize the bronchus or the bronchiole by using the peeled mucosa of the bronchus or the bronchiole.

A fourth specific example of the invention is to guide a spraying device to a part to be embolized in a bronchus or a bronchiole, and spray a spray material having a property to cause inflammation in a living tissue, in the part to be embolized, by means of the spraying device.

The medical device of the invention is desirably provided with a portion which artificially inflates and deflates a lung, a portion which embolizes and releases a bronchus or a bronchiole, and an observing portion which is provided in a pleural cavity in order to observe a surface of the lung with the bronchus or the bronchiole embolized by the embolizing and releasing portion and the lung inflated or deflated by the inflating and deflating portion. According to this construction, an operator can determine whether the bronchus is reliably embolized, by observing the surface of the lung through the observing portion, with the bronchus or the bronchiole artificially embolized by the embolizing and releasing portion and the lung artificially inflated or deflated by the inflating and deflating portion.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

FIGS. 3A and 3B show a use example of the bronchus embolization device of the first embodiment, FIG. 3A being a longitudinal sectional view of the portions showing the state in which a puncture portion of an injection device projected from a channel of a bronchoscope is made to puncture the mucosa of a bronchus to inject an injection material into a submucosa, and FIG. 3B being a longitudinal sectional view of the portions showing the state in which the internal cavity of the bronchus is narrowed by a plurality of swellings to completely embolize a target bronchus.

FIG. 4 is a schematic construction view showing the state of distribution of an affected part when a certain period of time elapses after the target bronchus is embolized by the use of the bronchus embolization device of the first embodiment.

FIGS. 5A and 5B show a second embodiment of the invention, FIG. 5A being a longitudinal sectional view of the portions showing the state in which an injection material different from that of the first embodiment is injected into the bronchial submucosa, and FIG. 5B being a longitudinal sectional view of the portions showing the state in which an injection material different from that, of FIG. 5A is injected into the bronchial submucosa.

FIG. 6 is a schematic construction view of a bronchus embolization device, showing a third embodiment of the invention.

FIGS. 16A to 16C show a sixth embodiment of the invention, FIG. 16A being a longitudinal sectional view of the portions showing a leading portion of a spray catheter of the spraying device, FIG. 16B being a longitudinal sectional view of the portions showing a proximal-end side of the spray catheter, and FIG. 16C being a longitudinal sectional view of the essential portions, showing a syringe.

FIG. 17 is a longitudinal sectional view of an embolization device of a sixth embodiment.

DETAILED DESCRIPTION OF THE INVENTION

Preferred embodiments of the present invention will be described hereinafter with reference to the drawings.

Figure 1:
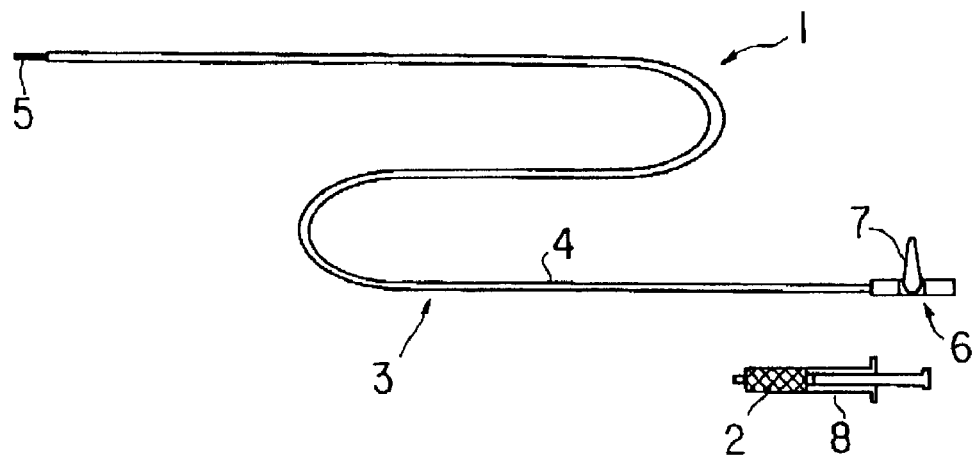
FIG. 1 is a plan view showing a bronchus embolization device of a first embodiment of the invention.

A first embodiment of the invention will be described below with reference to FIGS. 1 to 4. FIG. 1 shows a bronchus embolization device 1 which is a medical device according to the first embodiment for effecting treatment of lung emphysema by embolizing a bronchus. Incidentally, the embolization of a bronchus or a bronchiole can be utilized for the treatment of pneumothorax, lung tuberculosis and bronchus tuberculosis besides the treatment of lung emphysema. This bronchus embolization device 1 includes an injection device 3 for injecting an injection material (a shape change inducing portion) 2 to be injected into the submucosa of the bronchus, into the submucosa. This injection material 2 is desirably made of a highly viscous material, for example, bioadhesive such as fibrin adhesive, and collagen.

The injection device 3 is provided with an elongated tubular catheter 4. A sharp needle-like puncture portion 5 to puncture the mucosa of the bronchus is disposed in a leading end portion of the catheter 4. In addition, a manipulation portion 6 to be manipulated by an operator is disposed in a proximal portion of the catheter 4 on an operator side. This manipulation portion 6 is provided with a connection portion such as a three-way cock 7. A syringe 8, which contains an injection material 2, can be removably connected to the connection portion.

Incidentally, the injection device 3 may be constructed to have a sheath (not shown) fitted on the peripheral surface of the puncture portion 5 and that of the catheter 4 so that the puncture portion 5 can be moved into and out of a leading portion of the sheath.

Figure 2:
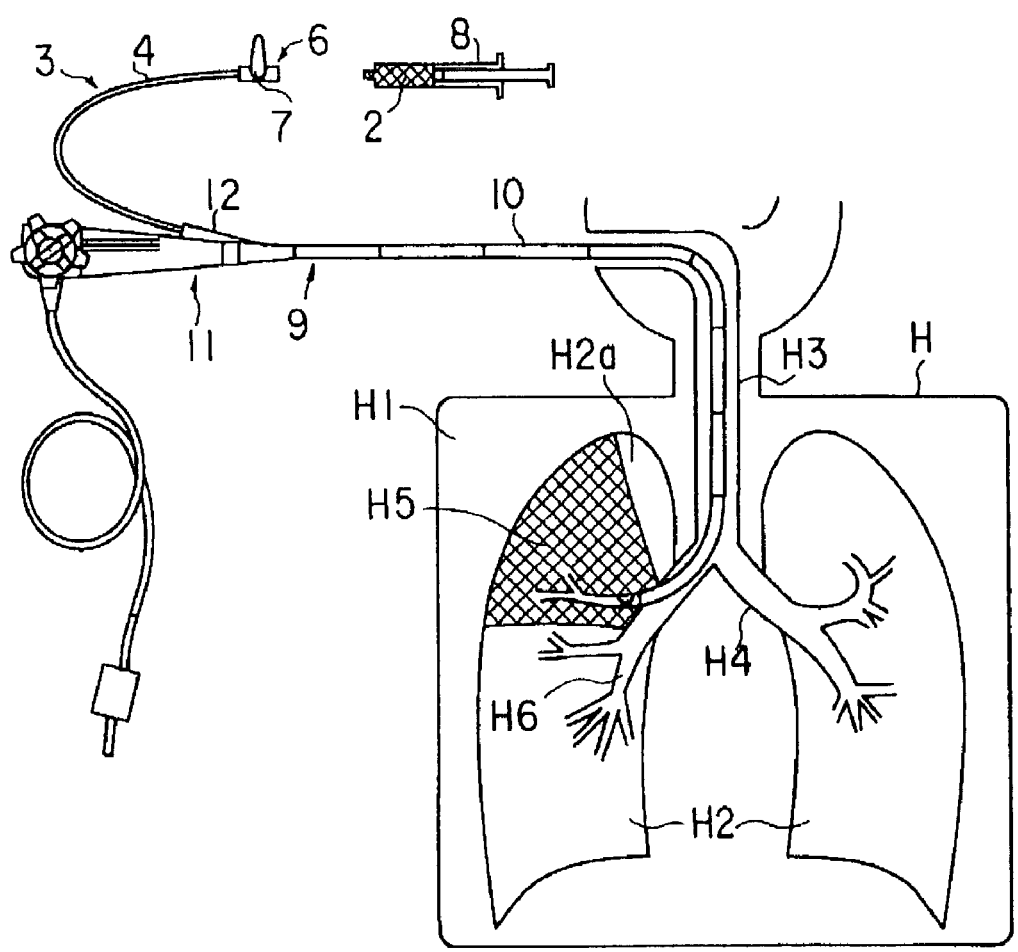
FIG. 2 is a schematic construction view showing a locally embolized state which is a use example of the bronchus embolization device of the first embodiment.

As shown in FIG. 2, during treatment of lung emphysema in a pleural cavity H1 of a patient H, a bronchoscope 9 is used in combination with the bronchus embolization device 1 of the first embodiment. This bronchoscope 9 is provided with an elongated inserting portion 10 to be inserted into the body of the patient H. A manipulation portion 11 is provided in a proximal portion of the inserting portion 10 on the operator side.

Furthermore, a channel 10c (refer to FIG. 7) through which to insert a treatment element is provided in the interior of the inserting portion 10 of the bronchoscope 9. A leading opening portion of this channel 10c is provided in a leading portion of the inserting portion 10. The manipulation portion 11 on the operator side is provided with a channel port portion 12, which communicates with a proximal portion of the channel 10c. The injection device 3 is to be inserted into the channel 10c of the bronchoscope 9 from the channel port portion 12.

The operation of the above-described construction will be described below. The following description will refer to the work of giving treatment to lung emphysema in the pleural cavity H1 of the patient H by means of the bronchus embolization device 1 of the first embodiment as shown in FIG. 2. Incidentally, in FIG. 2, symbol H2 denotes a lung, symbol H3 denotes a trachea, symbol H4 denotes a bronchus, symbol H5 denotes a lung-emphysema-affected part, and symbol H6 denotes a bronchus internal cavity.

At the time of treatment of lung emphysema in the pleural cavity H1 of the patient H, the inserting portion 10 of the bronchoscope 9 is in advance inserted into the bronchus H4 through the trachea H3, and the leading portion of the inserting portion 10 of the bronchoscope 9 is introduced into the bronchus internal cavity H6 which is regarded as a target. After that, the injection device 3 is introduced into the bronchus internal cavity H6 distributed in the lung-emphysema-affected portion H5, via the channel 10c of the bronchoscope 9.

FIGS. 3A and 3B are diagrammatic views showing a longitudinal section of the bronchus H4, illustrating the operation of the bronchus embolization device 1 of the first embodiment. As shown in FIG. 3A, after a leading portion of the bronchoscope 9 has reached the target bronchus internal cavity H6, the puncture portion 5 of the injection device 3 is projected from the channel 10c of the bronchoscope 9, and punctures a mucosa H7 of the bronchus H4. At this time, when the leading end of the puncture portion 5 reaches a submucosa H8 of the bronchus H4, the injection material 2 is injected into the submucosa H8 by the use of the syringe 8. The syringe 8, the elongated tubular catheter 4 and the hollow puncture portion 5 are filled with the injection material 2 beforehand. Some of the injection material 2 is injected into the submucosa H8 through the tip hole of the puncture portion 5 by the operation of the syringe 8.

The submucosa H8 which exists between the mucosa H7 of the bronchus H4 and a bronchus cartilage H9 is formed by a loosely bound tissue whose binding is not tight, and a comparatively amount of liquid substance can be injected into the submucosa H8. When the injection material 2 is injected into the submucosa H8, the injected part forms a swelling H10 toward the bronchus internal cavity H6 to narrow the bronchus internal cavity H6.

At this time, a plurality of swellings H10 are formed at different locations along the circumferential direction of the bronchus internal cavity H6 so that the plurality of swellings H10 formed at the different locations are joined together as shown in FIG. 3B, thereby completely embolizing the target bronchus H4. Incidentally, when the plurality of swellings H10 are to be formed, the puncture portion 5 of the injection device 3 is temporarily drawn from the mucosa H7 of the bronchus H4, and is newly made to puncture after having been shifted from the existing puncture portion to the right or left along the circumferential direction of the bronchus internal cavity H6.

When the bronchus internal cavity H6 distributed in the lung-emphysema-affected part H5 is completely embolized, the air stored in the lung-emphysema-affected part H5 is absorbed with time. Accordingly, as shown in FIG. 4, the volume of the lung-emphysema-affected part H5 decreases to a remarkable extent. Consequently, a pulmonary normal tissue H2a which has lost its ventilation function by being pressed by the lung-emphysema-affected portion H5 which occupied a large volume in the pleural cavity H1 of the patient H is released from pressurization by the deflation of the lung-emphysema-affected portion H5, whereby the ventilation function is restored. Thus, the respiratory function of the patient H is improved.

Therefore, the first embodiment having the above-described construction serves the following advantages. Namely, since the bronchus embolization device 1 of the first embodiment can be inserted into the target bronchus internal cavity H6 through the channel 10c of the bronchoscope 9, the first embodiment has the advantage that it is possible to give treatment to lung emphysema without a large invasion into the body of the patient H. Moreover, the injection material 2 and the delivery device 3 have simple constructions and low cost. Further, it is possible to repeatedly give treatment for lung emphysema. In addition, the first embodiment also has the advantage that an embolized portion does not move, unlike the case where foreign matter is placed in the bronchus internal cavity H6. Consequently, it is possible to reliably give treatment to lung emphysema with a small invasion.

FIG. 5A shows a second embodiment of the invention. The second embodiment has a construction in which the injection material 2 of the first embodiment (refer to FIGS. 1 to 4) is modified as follows.

Namely, the injection material 2 of the second embodiment has a construction in which a particulate substance 22 which is a solid component is suspended in a liquid base material 21 as shown in FIG. 5A. The constituent material of the injection material 2 is made of a material having good biocompatibility, which does not exhibit toxicity nor stimulus to a living tissue when the material is injected into the submucosa H8 of the bronchus H4. The particulate substance 22 contains a solid component of high biocompatibility, such as silicone, metal particles (such as titanium particles), apatite or β-TCP (tricalcium phosphate).

In the second embodiment, the constituent material of the injection material 2 used in the bronchus embolization device 1 for embolizing the bronchus H4 and giving treatment for lung emphysema has a construction in which the particulate substance 22, which is a solid component, is suspended in the liquid base material 21. Consequently, the second embodiment has the advantage that when the injection material 2 is injected into the submucosa H8 of the bronchus H4 by the injection device 3, the swollen shapes of the swellings H10 formed in the mucosa of the bronchus H4 are maintained for a long time. Therefore, since it is possible to lengthen the time period of embolization of the bronchus internal cavity H6 formed by the injection of the injection material 2, it is possible to increase the effect of treatment of lung emphysema.

As shown in FIG. 5B, the injection material 2 may also be made of a material which is held in the state of the liquid base material 21 at the time of injection, and changes to solid form or gel form of very high viscosity by addition of a curing agent 23 to the liquid base material 21 after injection. Otherwise, the injection material 2 may also be a powder or a solid, which expands and changes to gel form by absorbing water inside a living body, after having been injected into the living body. An example of a material which is small in volume in its dry state and expands to a very great extent by absorbing water is a poly (acrylic acid) salt bridge body. An example of a material, which has two forms, liquid form and gel form, is alginic acid. Alginic acid changes from liquid form to gel form under the presence of ions. An example of a material, which has two forms, liquid form and solid form, is a silicone resin. There exists a silicone resin (liquid) that solidifies by addition of a curing agent (liquid).

Figure 7:
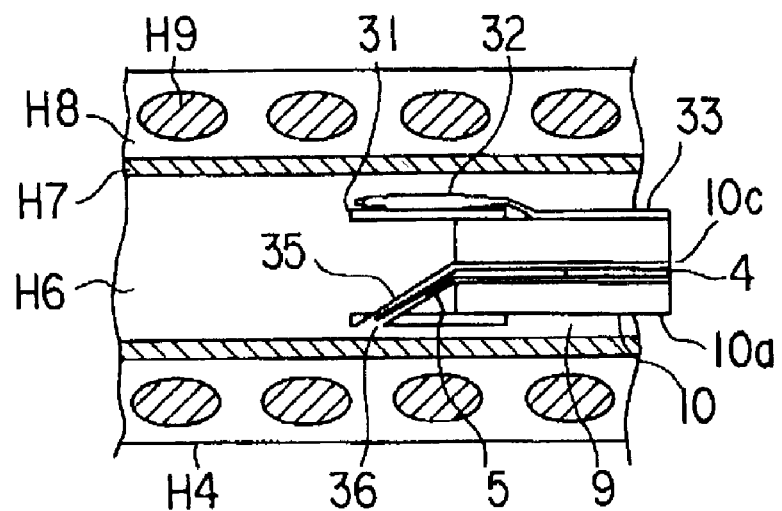
FIG. 7 is a longitudinal sectional view of the portions showing the state in which a leading portion of the embolization device of the third embodiment is inserted into the internal cavity of a bronchus.
Figure 8:
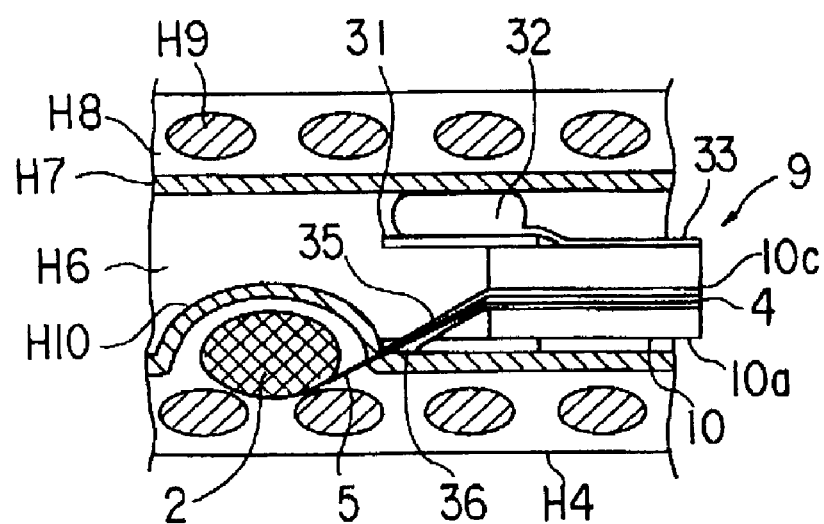
FIG. 8 is a longitudinal sectional view of the portions showing the state in which bronchus embolization is being performed by using the embolization device of the third embodiment.

FIGS. 6 to 8 show a third embodiment of the invention. The third embodiment has a construction in which the construction of the bronchus embolization device 1 of the first embodiment (refer to FIGS. 1 to 4) is modified as follows.

Namely, a cap 31, which assists in injection manipulation is provided at a leading portion 10a of the inserting portion 10 of the bronchoscope 9. An expandable balloon 32 is provided on one side of the peripheral surface of the cap 31. A leading portion of a thin tube 33, which is externally attached to the peripheral surface of the bronchoscope 9 is connected to the balloon 32. A proximal portion of the tube 33 is disposed to extend to the side of a manipulation portion 11 of the bronchoscope 9. In addition, a connection portion such as a three-way cock 34 is disposed at the proximal portion of the tube 33. The syringe 8 can be, removably connected to the connection portion.

FIG. 7 shows the inserted state of the leading portion 10a of the bronchoscope 9 inserted in the bronchus internal cavity H6. A sheath 35 for guiding the puncture portion 5 of the injection device 3 from the leading opening portion of the channel 10c of the bronchoscope 9 toward the leading end of the cap 31 is provided in the interior of the cap 31 attached to the leading portion 10a of the bronchoscope 9. A leading portion of this sheath 35 is connected to a puncture hole 36 provided in the leading portion of the cap 31.

The puncture hole 36 of the cap 31 is disposed on the opposite side to the balloon 32 provided on one side of the peripheral surface of the cap 31. Incidentally, in the case where the sheath 35 and the cap 31 are made of transparent materials, the operator can observe the position of the puncture portion 5 of the injection device 3 and the state of the mucosa H7 of the bronchus H4. Moreover, the third embodiment may also have a construction for adjusting the projecting length of the puncture portion 5 as by reducing the inside diameter of the leading portion of the sheath 35. The operation of the third embodiment having the above-described construction will be described below. FIG. 8 shows a state in which bronchus embolization is being performed by the use of the bronchus embolization device 1 of the third embodiment. The injection device 3 of the bronchus embolization device 1 is inserted into the airway of the patient H together with the bronchoscope 9. When the leading portion 10a of the bronchoscope 9 reaches the bronchus internal cavity H6 which is regarded as a target, air is fed to the tube 33 connected to the balloon 32, by the use of the syringe 8 or the like, thereby expanding the balloon 32. At this time, as shown in FIG. 8, the side surface of the cap 31 that is disposed on the opposite side to the balloon 32 is pressed against the mucosa H7 of the bronchus H4 by the expansion of the balloon 32. During this state, the leading portion 10a of the bronchoscope 9 does not vibrate in the bronchus internal cavity H6, and the puncture portion 5 of the injection device 3 is made to puncture the submucosa H8 of the bronchus H4 through the channel 10c, the sheath 35 and the puncture hole 36 of the cap 31.

In addition, after the leading end of the puncture portion 5 has reached the submucosa H8, the injection material 2 is injected into the submucosa H8 through the catheter 4. By adjusting the positional relationship between the puncture hole 36 of the cap 31 and the channel 10c and the projecting length of the puncture portion 5, it is possible to avoid a trouble which causes the leading end of the puncture portion 5 to pass through the bronchus cartilage H9 and project outward from the bronchus H4 or which allows the puncture portion 5 to puncture to a shallow depth at which the injection material 2 spills into the bronchus internal cavity H6.

Subsequently, a plurality of swellings H10 are formed at different locations along the circumferential direction of the bronchus internal cavity H6 by an operation similar to that of the first embodiment, and the plurality of swellings H10 are joined together as shown in FIG. 3B, whereby the target bronchus H4 can be completely embolized.

Consequently, the third embodiment having the above-described construction serves the following advantages. Namely, since the bronchus embolization device 1 of the third embodiment can be inserted into the target bronchus internal cavity H6 through the channel 10c of the bronchoscope 9, the third embodiment has the advantage that it is possible to give treatment to lung emphysema without a large invasion into the body of the patient H, similarly to the case of the first embodiment. Moreover, in the third embodiment, it is possible that the puncture portion 5 of injection device 3 punctures the submucosa H8 of the bronchus H4 under the condition that the side surface of the cap 31 is fixedly pressed against the mucosa H7 of the bronchus H4 because of the expansion of the balloon 32. Therefore, it is possible to easily define the depth and the position of injection of the puncture portion 5 of the injection device 3.

Figure 9A:
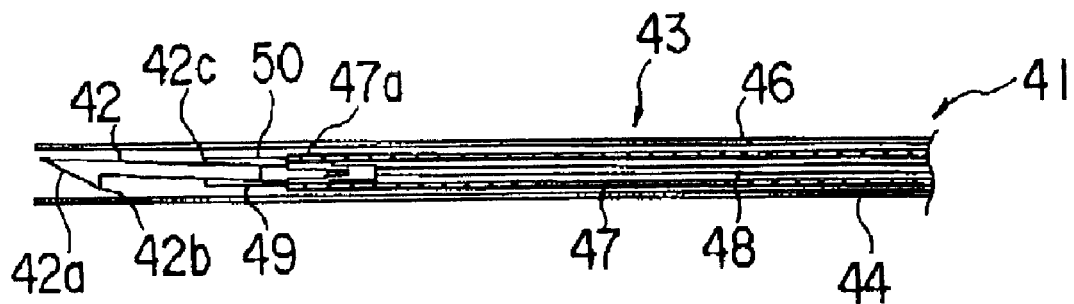
FIGS. 9A and 9B show an embolization device of a fourth embodiment, FIG. 9A being a longitudinal sectional view showing a leading portion of an elongated delivery device, and FIG. 9B being a longitudinal sectional view of the portions showing a handle portion of a proximal portion of the delivery device.
Figure 9B:
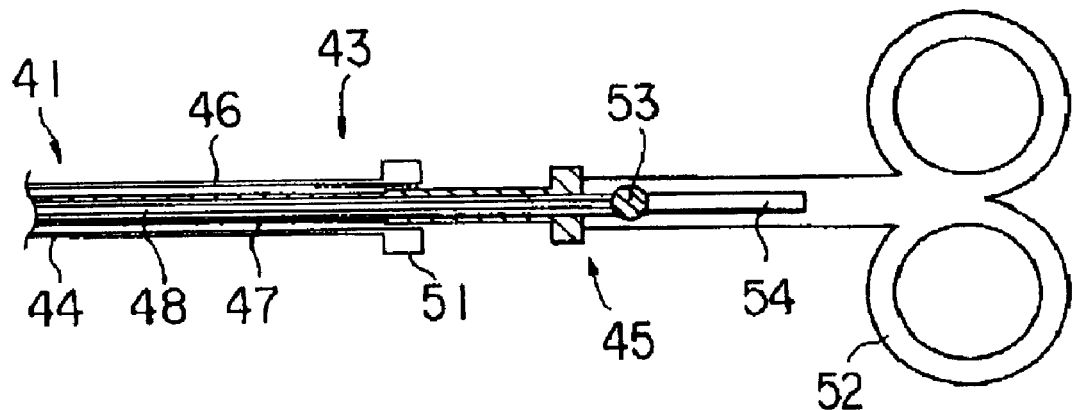

FIGS. 9A, 9B, 10A and 10B show a fourth embodiment of the invention. As shown in FIGS. 9A and 9B, a bronchus embolization device 41 of the fourth embodiment as shown in FIGS. 9A and 9B, includes an approximately stick-shaped placing object 42 and an elongate delivery device 43 which inserts the placing object 42 into the body.

The delivery device 43 includes an inserting portion 44 having an elongated double tube structure and an operator-side manipulation portion 45 disposed at a proximal portion of the inserting portion 44. The double tube of the inserting portion 44 is provided with a guide tube 47 and a sheath 46 axially movably fitted to the outside of the guide tube 47. Further, a manipulation wire 48 is axially movably inserted in the interior of the guide tube 47.

A placing object holding portion 49 for holding the placing object 42 is provided at a leading portion of the inserting portion 44. The placing object holding portion 49 is provided with a pair of holding portion elements 50 for fixedly clamping the placing object 42. The pair of holding portion elements 50 are made of a thin plate-like material and are constructed to open outwardly in the direction of their leading ends. Furthermore, a proximal portion of each of the holding portion elements 50 is connected to a leading portion of the manipulation wire 48.

The operator-side manipulation portion 45 is provided with a flange-shaped proximal portion element 51 connected to a proximal portion of the sheath 46, a handle 52 connected to a proximal portion of the guide tube 47, and a manipulation knob 53 connected to a proximal portion of the manipulation wire 48. The manipulation knob 53 is supported for movement along a slot 54 formed to extend in the handle 52 in the axial direction thereof.

A leading portion 47a of the guide tube 47 overlaps a proximal portion of each of the holding portion elements 50. When the manipulation knob 53 is made to move back and forth, the holding portion elements 50 are made to move into and out of the leading portion 47a of the guide tube 47 via the manipulation wire 48. At this time, as a portion where the holding portion elements 50 overlap the leading portion 47a of the guide tube 47 becomes larger, the degree of opening of the leading portions of the holding portion elements 50 becomes smaller, thereby firmly holding the placing object 42. As the portion where the holding portion elements 50 overlap the leading portion 47a of the guide tube 47 becomes smaller, the degree of opening of the leading portions of the holding portion elements 50 becomes larger, thereby releasing the placing object 42.

Figure 10A:
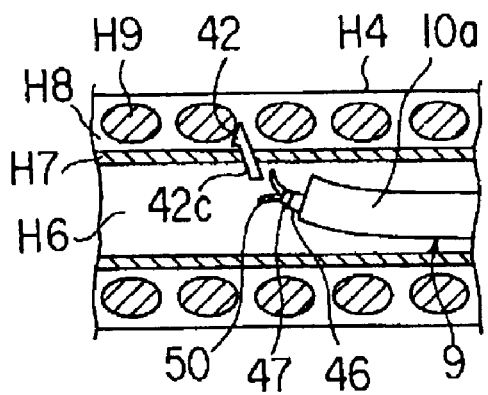
FIG. 10A is a longitudinal sectional view of the portions showing the state in which the placing object is made to puncture the internal cavity of the bronchus by the embolization device of the fourth embodiment.

Formed at a leading portion of the placing object 42 is a sharp puncture portion 42a which punctures the mucosa H7 of the bronchus H4, the submucosa H8 and the bronchus cartilage H9 as shown in FIG. 10A. This puncture portion 42a has an anchor-like shape having a claw 42b for preventing the placing object 42 from coming off after having punctured a living tissue. A proximal portion of the placing object 42 is provided with a biological reaction acceleration portion 42c which is to be held in the state of being projected into the bronchus internal cavity H6. A portion that stimulates the living body can accelerate biological reactions thus can perform as a biological reaction acceleration portion. A portion that injures the bronchus mucosa, like the puncture portion 42a shown in FIG. 10A, or has an undulated shape that stimulates the bronchus mucosa usually accelerate biological reactions. As shown in FIG. 10A, the placing object 42 is held with the sharp puncture portion 42a in the state of puncturing the mucosa H7 of the bronchus H4, the submucosa H8 and the bronchus cartilage H9 and with the biological reaction acceleration portion 42c in the state of being projected into the bronchus internal cavity H6. At this time, the placing object 42 is prevented from vibrating and coming off in the bronchus internal cavity H6, because the puncture portion 42a secures the placing object 42.

Incidentally, the placing object 42 may have other shapes, such as the shape of a clip, which is normally used with an endoscope and is firmly fixed to the mucosa H7 of the bronchus H4. It is desirable that at least a part of the constituent material of the placing object 42 have a nature, which proliferates the tissue of the mucosa H7 of the bronchus H4 by forming a granulation tissue such as a chitinous tissue.

The proximal portion element 51 of the proximal portion of the sheath 46 can be moved with respect to the handle 52 along the axial direction of the guide tube 47. By moving the proximal portion element 51 of the sheath 46 along the axial direction of the guide tube 47, it is possible to move the placing object holding portion 49 into and out of the leading portion of the sheath 46.

The operation of the fourth embodiment having the above-described construction will be described below. When the bronchus embolization device 41 of the fourth embodiment is to be used, the bronchus embolization device 41 is prepared so that the placing object holding portion 49 is accommodated in the sheath 46 as shown in FIG. 9A with the placing object 42 held by the placing object holding portion 49 of the delivery device 43.

After the completion of the preparation of the bronchus embolization device 41, the bronchoscope 9 is inserted into the bronchus H4 of the patient H. Then, after the bronchoscope 9 reaches a target part, the delivery device 43 of the bronchus embolization device 41 is inserted into the channel 10c of the bronchoscope 9.

After that, a leading portion of the delivery device 43 is projected into the bronchus internal cavity H6 from a channel opening portion of the leading portion 10a of the bronchoscope 9. At this time, the placing object holding portion 49 is held in the state of remaining accommodated in the sheath 46.

Then, the sheath 46 is drawn toward its proximal end by the handle 52 being manipulated with the leading portion of the delivery device 43 directed to the target part, whereby the placing object holding portion 49 is exposed out of the sheath 46. During this state, subsequently, the leading portion 10a of the bronchoscope 9 and the leading portion of the delivery device 43 are manipulated to be pushed out toward the leading end of the bronchus embolization device 41, thereby causing the placing object 42 to puncture the mucosa H7 of the bronchus H4, the submucosa H8 and the bronchus cartilage H9.

When the placing object 42 is made to puncture to a sufficient depth, the handle 52 is manipulated to push out the manipulation knob 53. As the holding portion elements 50 are moved by this manipulation in a direction in which to draw the holding portion elements 50 from the leading portion 47a of the guide tube 47, the portion where the guide tube 47 and the holding portion elements 50 overlap each other becomes smaller, and the degree of opening of the leading portions of the holding portion elements 50 becomes larger, thereby releasing the placing object 42. Thus, as shown in FIG. 10A, the placing object 42 is placed in the target part of the bronchus H4. At this time, the biological reaction acceleration portion 42c of the proximal portion of the placing object 42 is held in the state of being projected into the bronchus internal cavity H6.

Figure 10B:
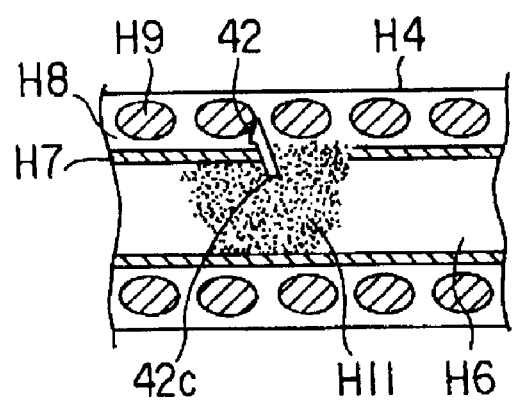
FIG. 10B is a longitudinal sectional view of the portions showing the state of the bronchus when a certain period of time elapses after the placing object is placed.

During this state, a biological reaction centered about the biological reaction acceleration portion 42c of the placing object 42 takes place in the bronchus internal cavity H6, whereby a granulation tissue H11 is formed. Then, when a certain period of time passes after the placing object 42 has been placed, the bronchus internal cavity H6 is embolized by the granulation tissue H11 formed about the biological reaction acceleration portion 42c of the placing object 42 as shown in FIG. 10B.

Accordingly, in the bronchus embolization device 41 according to the fourth embodiment having the above-described construction, it is possible to place the placing object 42 in the target part of the bronchus H4 by inserting the delivery device 43 into the target bronchus internal cavity H6 through the channel 10c of the bronchoscope 9. In addition, it is possible to embolize the bronchus internal cavity H6 by the granulation tissue H11 formed about the biological reaction acceleration portion 42c of the placing object 42. Therefore, similarly to the first embodiment, the fourth embodiment has the advantage that it is possible to give treatment to lung emphysema without a large invasion into the body of the patient H. Moreover, the fourth embodiment has the advantage that the placing object 42 and the delivery device 43 can be made simple in construction.

FIGS. 11A, 11B, 12A and 12B show a bronchus embolization device according to a fifth embodiment of the invention. The bronchus embolization device of the fifth embodiment includes a treatment device 61 for giving surgical treatment such as dissection, peeling and suture to the mucosa H7 of the bronchus H4.

Figure 11A:
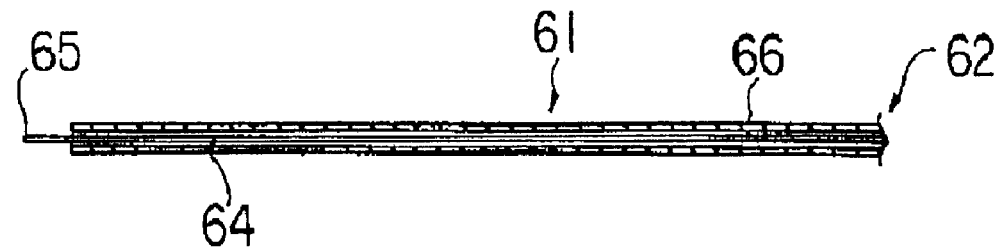
FIGS. 11A and 11B show an embolization device of a fifth embodiment of the invention, FIG. 11A being a longitudinal sectional view of the portions showing a leading portion of an elongated delivery device, and FIG. 11B being a longitudinal sectional view of the portions showing a handle portion of a proximal portion of the delivery device.

The treatment device 61 is provided with an elongated inserting portion 62 capable of being inserted into a channel of the bronchoscope 9 and an operator-side manipulation portion 63 disposed at a proximal portion of the inserting portion 62. Further, a wire-like shaft portion 64 is provided in the inserting portion 62. As shown in FIG. 11A, a treatment portion 65 having a shape such as an injection needle, a knife, a spatula or a bowl is connected to a leading portion of the unapertured region 64. The treatment portion 65 and the shaft portion 64 are covered with a sheath 66.

Figure 11B:
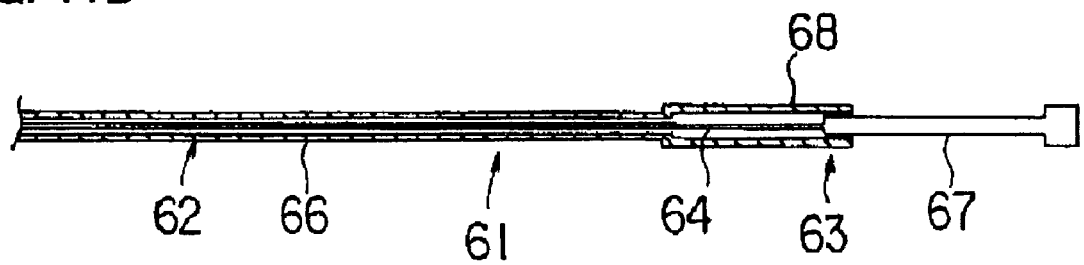

As shown in FIG. 11B, the operator-side manipulation portion 63 is provided with a manipulation shaft portion 67 connected to a proximal portion of the shaft portion 64 and a tubular manipulation tube portion 68 connected to a proximal portion of the sheath 66. The manipulation shaft portion 67 and the manipulation tube portion 68 can be moved forward and backward with respect to each other.

The operation of the fifth embodiment having the above-described construction will be described below. When the treatment device 61 of the fifth embodiment is to be used, the knife-shaped treatment portion 65 is in advance fitted to a leading portion of the shaft portion 64 of the treatment device 61. The inserting portion 62 of the treatment device 61 is inserted into a channel of the bronchoscope 9 and reaches the target bronchus internal cavity H6.

Figure 12A:
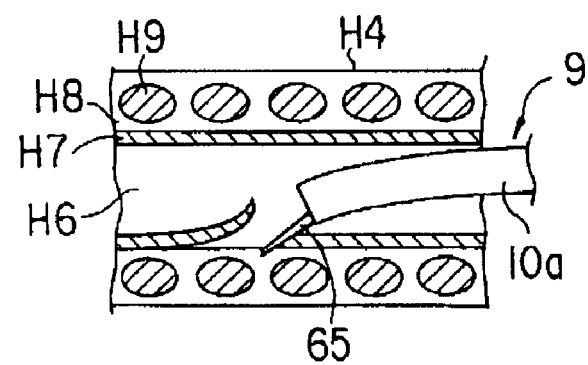
FIG. 12A is a longitudinal sectional view of the portions showing a knife-shaped treatment element of the embolization device of the fifth embodiment.

After that, a leading portion of the inserting portion 62 of the treatment device 61 is projected into the bronchus internal cavity H6 from a channel opening portion of the leading end portion 10a of the bronchoscope 9. Then, as shown in FIG. 12A, the mucosa H7 of the bronchus H4 is dissected around its entire circumference by the knife-shaped treatment portion 65 of the treatment device 61, whereby the mucosa H7 of the bronchus H4 is peeled from the bronchus cartilage H9.

Figure 12B:
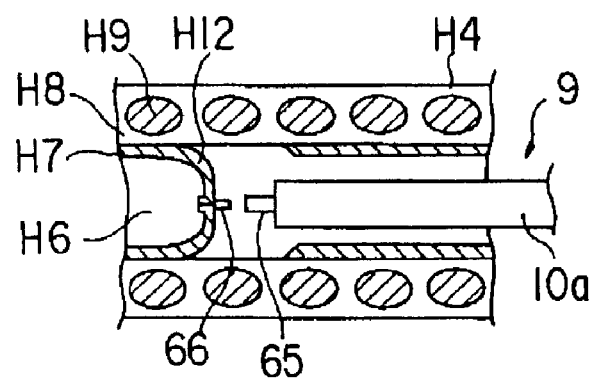
FIG. 12B is a longitudinal sectional view of the portions showing the state in which a tip portion of a leaf of the mucosa of the bronchus is sutured with a clip and the bronchus internal cavity is completely embolized.

Thus, after a leaf H12 has been formed with a cut portion of the mucosa H7 of the bronchus H4 in the bronchus internal cavity H6, as shown in FIG. 12B, a leading portion of the leaf H12 of the mucosa H7 of the bronchus H4 is sutured with a clip 66, thereby completely embolizing the bronchus internal cavity H6. The clip 66 is similar to those used for stanching blood in an endoscopic procedure, the construction and use of which is well known in the art.

Incidentally, a peeling method for peeling the mucosa H7 of the bronchus H4 from the bronchus cartilage H9 may also be a local injection to the submucosa H8 or a peeling manipulation using forceps. The sutured part of the mucosa H7 of the bronchus H4 is cured with the elapse of time.

Therefore, the treatment device 61 of the bronchus embolization device according to the fifth embodiment having the above-described construction can be inserted into the target bronchus internal cavity H6 through the channel 10c of the bronchoscope 9, so that similarly to the first embodiment, the fifth embodiment has the advantage that it is possible to give treatment to lung emphysema without a large invasion into the body of the patient H.

Figure 13:
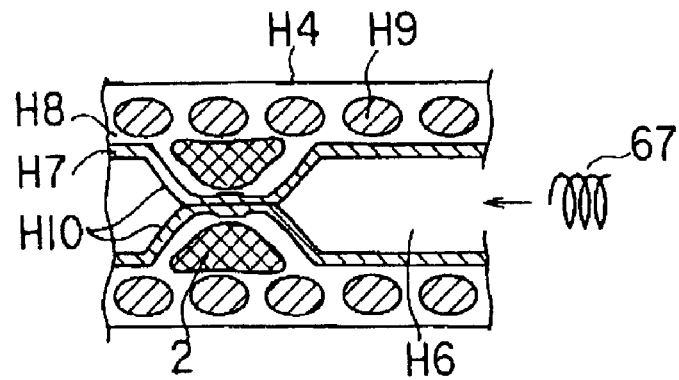
FIG. 13 is a longitudinal sectional view of the portions showing a modification of the embolization device of the fifth embodiment.
Figure 14:
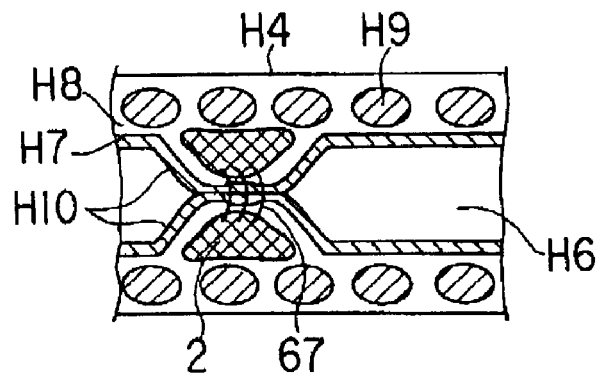
FIG. 14 is a longitudinal sectional view of the portions showing the state in which each closely adhered portion of the plurality of swellings is fixed with a coil in the modification of the embolization device of the fifth embodiment.
Figure 15:
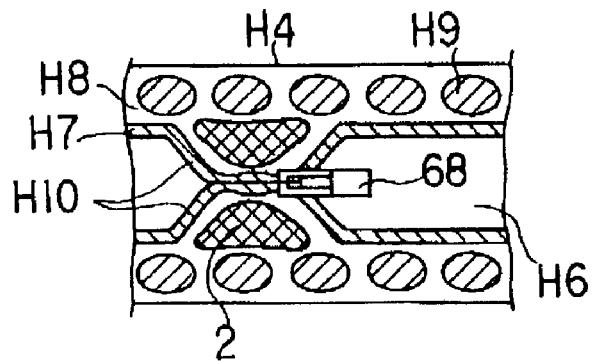
FIG. 15 is a longitudinal sectional view of the portions showing the state in which each closely adhered portion of the plurality of swellings is fixed with a clip in the modification of the embolization device of the fifth embodiment.

FIGS. 13 to 15 show a modification of the fourth embodiment (refer to FIGS. 9A, 9B, 10A and 10B). In this modification, the liquid-like injection material 2 is injected into the submucosa H8 by the use of an injection device so that the mucosa H7 of the bronchus H4 into the bronchus internal cavity H6 is projected to form the swelling H10.

In this manner, a plurality of swellings H10 are formed as shown in FIG. 13, and the plurality of swellings H10 of the mucosa H7 of the bronchus H4 are closely adhered to each other. After that, each closely adhered portion of the plurality of swellings H10 is fixed with a coil 67 as shown in FIG. 14 or a clip 68 as shown in FIG. 15 so that the closely adhered portions of the mucosa H7 of the bronchus H4 do not come off.

In FIG. 14, the tip of the coil is inserted into the swelling H10 of the mucosa H7 using the holding device, like the holding portion 50 shown in FIG. 10A, then the holding device rotates the coil so that it advances forwardly. Therefore the coil fixes the swellings.

In FIG. 15, a clip used for blood staunch under the endoscopic operation is used.

FIGS. 16A, 16B, 16C and 17 show a sixth embodiment of the invention. In the sixth embodiment, the treatment device for giving treatment to lung emphysema includes the spraying device 71 shown in FIGS. 16A and 16B and the bronchus embolization device 72 shown in FIG. 17.

The spraying device 71 is provided with an elongated spray catheter 73. A plurality of ejection holes 74 are formed in the leading end of the spray catheter 73 as shown in FIG. 16A. In addition, a spray material injection hole 75 is provided on the proximal-end side of the spray catheter 73. A three-way cock 76 is disposed in the injection hole 75, and a syringe 78 for injecting a spray material 77 or the like is removably connected to the spray material injection hole 75. Incidentally, the spray material 77 is a liquid- or power-like substance, and has a property to cause inflammation in a living tissue. An example of a material having this property is talc. The spray material 77 injected by the syringe 78 is ejected in atomized form from the ejection holes 74 of the spray catheter 73 with the syringe 78 or the like connected to the spray material injection hole 75.

In addition, a balloon 79 is provided for preventing the spray material 77 from spreading toward a bronchial central side behind the ejection holes 74 in a leading portion of the spray catheter 73. Furthermore, a spray channel 73a which connects the ejection holes 74 and the spray material injection hole 75 and an air channel 73b, which supplies air to the balloon 79, are provided in the interior of the spray catheter 73. An air injection port 80 is provided in a proximal portion of the air channel 73b. A three-way cock 81 is disposed in the air injection port 80.

In FIG. 17, the bronchus embolization device 72 includes a placing object 82, and a delivery device 83 for inserting the placing object 82 into the body. The placing object 82 is constructed to adhere closely to the mucosa of the bronchus and completely embolize the internal cavity of the bronchus, and is made of, for example, a balloon and sponge or the like. Examples of placing objects are disclosed in co-pending U.S. application Ser. No. 10/198,778, entitled "MEDICAL EMBOLIZATION ELEMENT AND METHOD OF EMBOLIZING TUBULAR ORGAN," the contents of which are incorporated herein by its reference.

The delivery device 83 is provided with a holding element 84 for holding the placing object 82 and an elongated sheath 85 disposed at the outside of the holding element 84. The holding element 84 is provided with a holding portion 87, such as grasper jaws, for holding the placing object 82 at a leading portion of an elongated shaft 86. In addition, a handle 88 for manipulating the holding portion 87 is provided at a proximal portion of the shaft 86. In this delivery device 83, the holding portion 87 at the leading end of the holding element 84 can move into and out of the sheath 85, and can be made to hold and release the placing object 82 by manipulating the handle 88 on the operator side. Incidentally, in the sixth embodiment, the delivery device 83 is constructed to serve also as a retrieving device, which retrieves the placing object 82.

The operation of the sixth embodiment having the above-described construction will be described below. In the sixth embodiment, as shown in FIG. 2, the spray catheter 73 of the spraying device 71 is introduced into the bronchus internal cavity H6 distributed in the lung-emphysema-affected portion H5, via the channel 10c of the bronchoscope 9 introduced into the bronchus internal cavity H6 in advance.

After that, the spray material 77 to be injected by the use of the syringe 78 is ejected in an atomized form from the ejection holes 74 of the spray catheter 73 with the syringe 78 and the like connected to the spray material injection hole 75 of the spray catheter 73. At this time, the spray material 77 sprayed into the bronchus internal cavity H6 distributed in the lung-emphysema-affected portion H5 spreads into the bronchus in the peripheral portion of the sprayed part and causes embolization of a peripheral airway and deflation of a tissue, which accompanies curing of inflammation, thereby deflating the lung-emphysema-affected portion H5 in time.

Immediately after the spraying of the spray material 77, the placing object 82 is placed at the central side of the part sprayed by the use of the delivery device 83 of the bronchus embolization device 72. In this manner, the spray material 77 is prevented from flowing back into a bronchus distributed in a healthy lung.

In addition, immediately before the placing object 82 is placed, the affected part H5 may also be deflated to some extent by sucking air by the use of a balloon catheter or the like and making a negative pressure in the bronchial internal cavity in which the placing object 82 is to be placed.

After the deflation of the lung-emphysema-affected portion H5 sufficiently proceeds and the spray material 77 is buried in the deflated tissue, the placing object 82 is retrieved and removed by the use of the holding element 84 of the delivery device 83, which also serves as a retrieving device.

Consequently, the sixth embodiment having the above-described construction has the advantage that the spraying device 71 of the treatment device and the delivery device 83 of the bronchus embolization device 72 can be inserted into the target bronchus internal cavity H6 through the channel 10c of the bronchoscope 9, so that it is possible to give treatment to lung emphysema without a large invasion into the body of the patient H, similarly to the case of the first embodiment. Moreover, in the sixth embodiment, it is possible to stably deflate the lung-emphysema-affected portion H5.

The invention is not limited to the above-described embodiment. For example, the placing object and the injection material of the embolization device used in the above-described embodiment may be made of a biocompatible material. In addition, when the injection material is to be injected into a bronchial submucosa, a guide using ultrasonic tomography or the like may also be used together to confirm the depth of puncture. This technique is performed under observation with the bronchoscope, but can also be performed under X-ray radioscopy. The bronchoscope may have a hard inserting portion instead of the flexible inserting portion shown in FIGS. 16A to 17.

Figure 18:
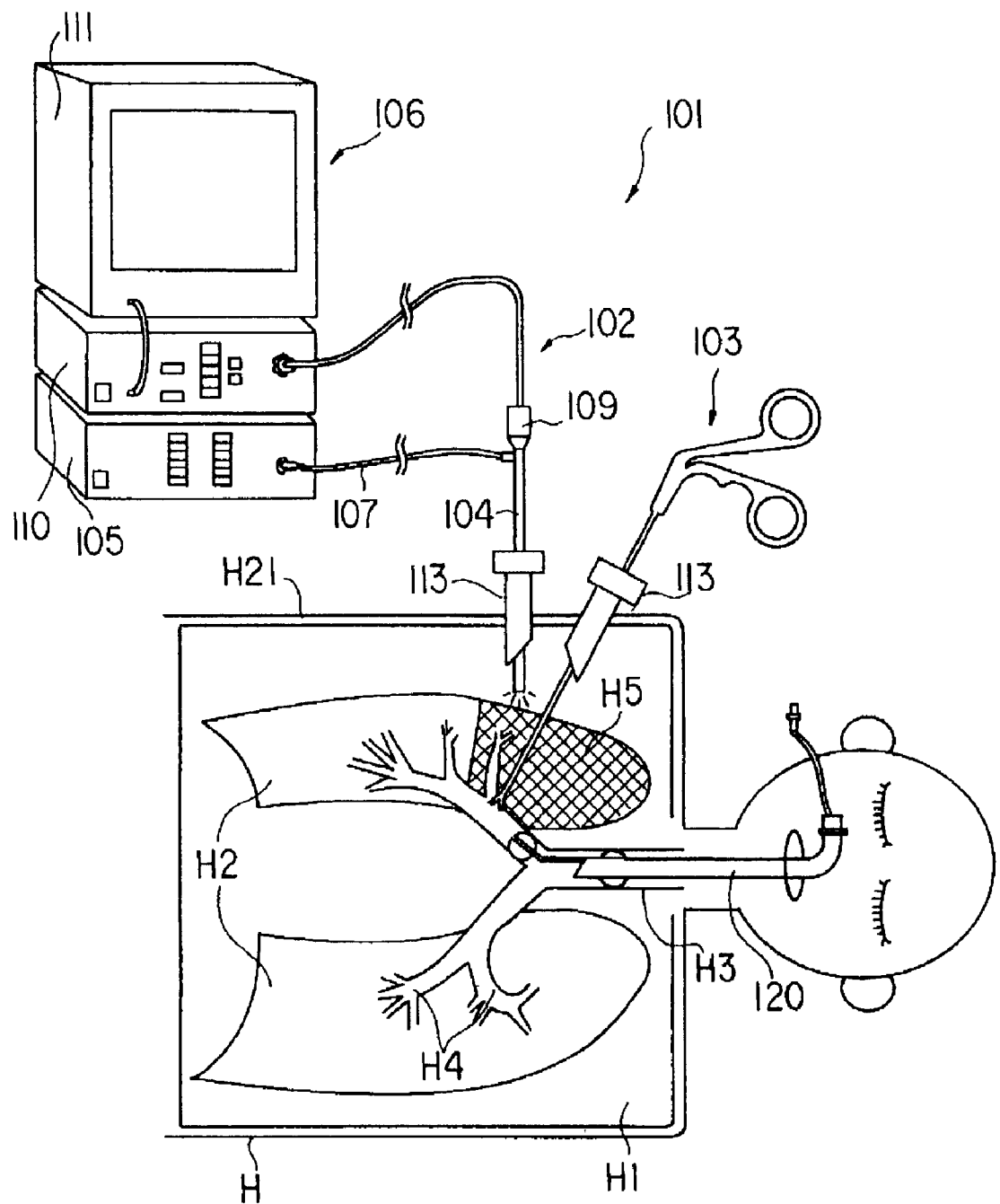
FIG. 18 is a schematic sectional view showing the state of use of a bronchus embolization device of a seventh embodiment.
Figure 19:
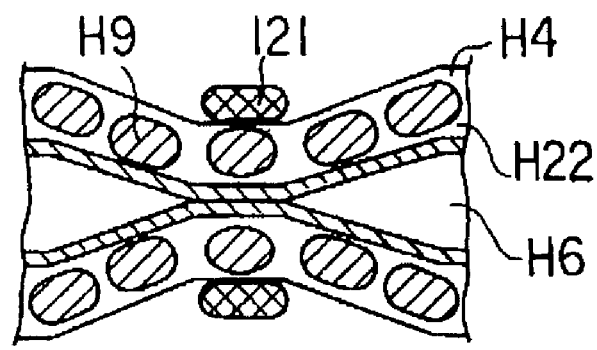
FIG. 19 is a longitudinal sectional view of a bronchus embolized by the bronchus embolization device of the seventh embodiment.

FIGS. 18 and 19 show a seventh embodiment of the invention. FIG. 18 shows the state of use of a bronchus embolization device 101 of the seventh embodiment, by using a schematic view of the pleural cavity H1 of a human being. The bronchus embolization device 101 includes an observation device 102 and a treatment device 103 which are used while being inserted into the pleural cavity H1 of the patient H.

The observation device 102 includes an endoscope and peripherals thereof, and is made of, for example, an optical viewing tube 104, a light source device 105 and a television camera system 106. The light source device 105 has a built-in lamp, which emits illumination light. The light source device 105 and the optical viewing tube 104 are connected to a light guide cable 107. The light of the lamp is guided from the light source device 105 to a leading portion of the optical viewing tube 104 via the light guide cable 107.

An image at the leading portion can be observed at a proximal portion of the optical viewing tube 104, and the television camera system 106 is connected to the proximal portion. The television camera system 106 is made of a camera head 109 connected to the optical viewing tube 104, a television camera device 110 connected to the camera head 109, and a television monitor 111 for displaying an image processed by the television camera device 110. An image at the leading end of the optical viewing tube 104 can be observed on the television monitor 111 via the television camera system 106.

The treatment device 103 is made of, for example, a surgical operation element having an elongated shaft portion. Specifically, there are various treatment elements having various shapes for surgical operations under endoscopes, such as forceps, scissors and clips. Incidentally, the optical viewing tube 104 and the treatment device 103 reach the inside of the pleural cavity H1 by being inserted into a trocar 113 disposed to puncture a chest wall H21 in the state of being inserted therethrough.

The endoscope used as the observation device 102 may be a video endoscope having a camera disposed at its leading end portion, in addition to the endoscope having the above-described construction. The endoscope may also be an endoscope having a flexible inserting portion (flexible scope), instead of an endoscope having a linear construction in which an inserting portion to be inserted into the body of a patient is rigid (rigid scope).

The operation of the seventh embodiment having the above-described construction will be described below. When the bronchus embolization device 101 according to the seventh embodiment is to be used, first of all, the trocar 113 is made to puncture the chest wall H21 of the patient H, to ensure an insertion port for the optical viewing tube 104 and the treatment device 103.

During this state, the optical viewing tube 104 and the treatment device 103 are inserted into the trocar 113, and are made to reach the interior of the pleural cavity H1. After that, the operator confirms the lung-emphysema-affected portion H5 while observing the state of the interior of the pleural cavity H1 through the optical viewing tube 104. Subsequently, the treatment of embolizing the bronchus H4 distributed in the lung-emphysema-affected portion H5 is performed by the use of the treatment device 103.

The treatment of embolizing the bronchus H4 is performed by the use of the treatment device 103 which has, for example, a leading end having the shape of forceps. In this case, after blood vessels and other tissues lying around the bronchus H4 and the bronchus H4 have been separated from each other to expose the external surface of the bronchus H4, the bronchus H4 can be ligatured from the outside by using a clip 121 or a comparatively thick thread-like material, as shown in FIG. 19.

FIG. 19 shows the state of embolization of the bronchus H4. In FIG. 19, a bronchus wall H22 is pressed toward the bronchus internal cavity H6 from the outside of the bronchus H4 by the clip 121, so that the bronchus wall H22 is closely sealed to embolize the bronchus internal cavity H6. The clip 122 can be an ordinary surgical clip, the construction of which is well known in the art. The clip 122, held by forceps, is placed at the embolization position, and pressed to deform so that the embolization is completed.

As means for similarly embolizing the bronchus H4 from the outside, the bronchus internal cavity H6 may be brought to an embolized state by using a device which clamps and presses the bronchus H4, and the bronchus internal cavity H6 may be vertically sutured to maintain the embolized state, by a plurality of clips.

In addition, when the bronchus H4 distributed in the lung-emphysema-affected portion H5 is embolized as described above, the flow of new air into the lung-emphysema-affected portion H5 is cut off. At this time, although a large amount of air is stored in the lung-emphysema-affected portion H5, the air is gradually absorbed with the elapse of time, and the volume of the lung-emphysema-affected portion H5 decreases to a remarkable extent. Thus, it is possible to obtain an advantage similar to lung volume reduction surgery.

In addition, by using the above-described construction, the operator can give treatment while viewing the surface of the lung H2 through the optical viewing tube 104. When the operator is to confirm whether a part to be embolized in the bronchus H4 is distributed in the lung-emphysema-affected portion H5 as shown in FIG. 18, for example during a surgical operation, the operator inserts a trachea tube 120 into the trachea H3 of the patient H and causes the patient H to inhale air or oxygen through the trachea tube 120, whereby the operator can view the state of inflation and deflation of the lung H2.

In the case where a trocar having a seal mechanism is used as the trocar 113, it is possible to make a positive pressure in the interior of the pleural cavity H1 and actively deflate the lung H2. Consequently, in this case, by removing the air stored in the lung-emphysema-affected portion H5 as completely as possible to reduce the volume of the lung-emphysema-affected portion H5 before the embolization of the bronchus H4, it is possible to hold the respiratory state of the lung-emphysema-affected portion H5 of the patient H in a comparatively good state immediately after treatment.

Therefore, the seventh embodiment having the above-described construction serves the following advantages. Namely, with the bronchus embolization device 101 of the seventh embodiment, the operator can ligate the bronchus H4 from the outside by manipulating the clip 121 or a comparatively thick thread-like material by the treatment device 103 to be inserted into the pleural cavity H1 through the trocar 113 made to puncture the chest wall H21, while viewing the surface of the lung H2 through the optical viewing tube 104, whereby the operator can embolize the bronchus H4 distributed in the lung-emphysema-affected portion H5. Consequently, similarly to the first embodiment, the seventh embodiment also has the advantage that it is possible to give treatment to lung emphysema without a large invasion into the body of the patient H. Moreover, in the seventh embodiment, since the operator can observe the surface of the lung H2 through the optical viewing tube 104, the operator can easily confirm a part to be embolized in the bronchus H4.

Figure 20:
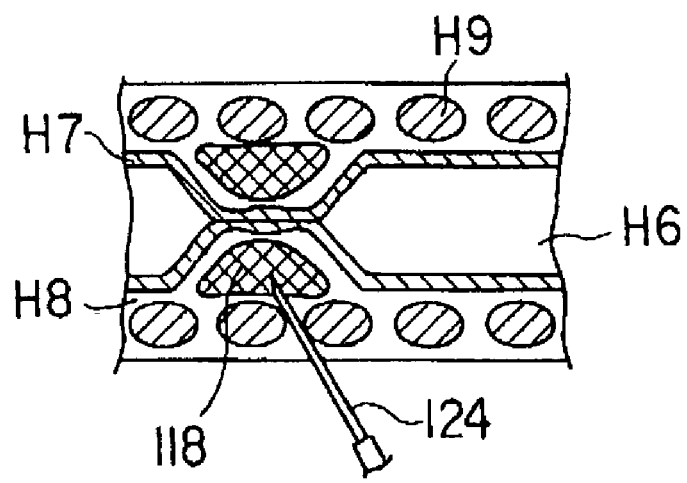
FIG. 20 is a longitudinal sectional view of the essential portions, showing a modification of a bronchial embolization method using the bronchus embolization device of the seventh embodiment.

As another method of embolizing the bronchus H4, there is a method of placing an embolization material (injection material) 118 in the bronchus wall H22 of the bronchus H4 as shown in FIG. 20. The method shown in FIG. 20 uses an injection device having a needle 124 at its leading end, as the treatment device 103. In this method, when the liquid embolization material 118 is injected with the needle 124 disposed to puncture the interior of the bronchus wall H22, for example, the submucosa H8 of the bronchus H4, the mucosa H7 of the bronchus H4 is projected into the bronchus internal cavity H6, whereby the bronchus internal cavity H6 can be embolized.

Figure 21:
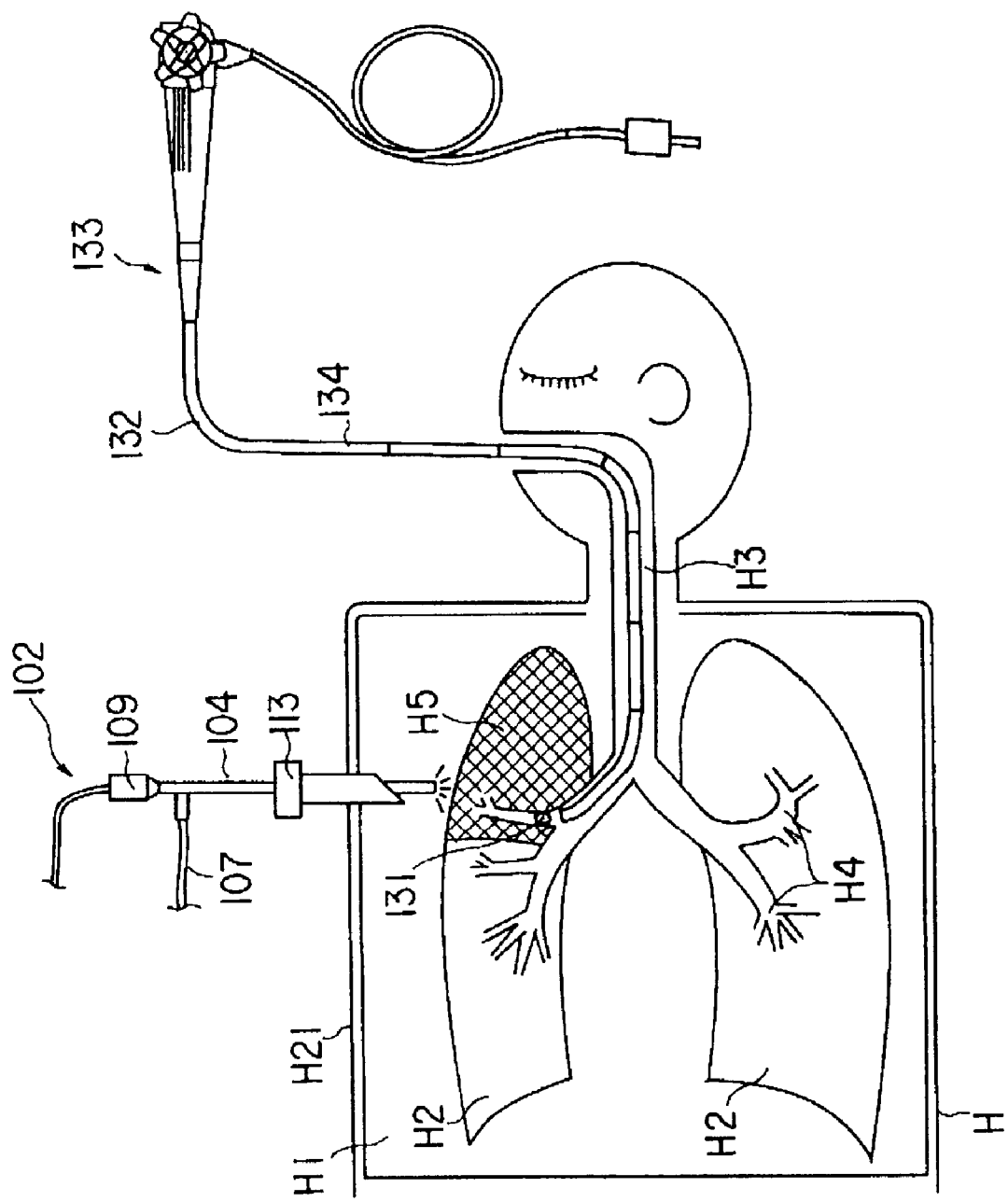
FIG. 21 is a schematic construction view showing the state of use of a bronchus embolization device of an eighth embodiment of the invention.

FIG. 21 shows an eighth embodiment of the invention. The eighth embodiment has a construction in which a part of the bronchus embolization device 101 of the seventh embodiment (refer to FIGS. 18 and 19) is modified as follows.

Namely, the eighth embodiment includes, instead of the treatment device 103 to be inserted into the pleural cavity H1 through the trocar 113 made to puncture the chest wall H21 as in the seventh embodiment, an embolization element placing device 133 which is made of an embolization element 131 to be placed in the bronchus H4 to completely embolize the bronchus internal cavity H6, and a delivery device 132 to be inserted into the bronchus H4 to guide the embolization element 131 to a placement position. In the eighth embodiment, the embolization element 131 may have any shape that adheres closely to the bronchus internal cavity H6, for example, a simple tubular shape, a tube-like shape, a sponge-like shape, a balloon-like shape and other shapes.

The delivery device 132 is constructed so that it is to be inserted into the bronchus H4 while it holds the embolization element 131 at its leading portion, the embolization element 131 may be clamped or accommodated inside of the delivery device,132 during the insertion. Otherwise, The delivery device has a channel that guides the embolization element 131 into its leading end portion after having been inserted into the bronchus internal cavity H6. In the eighth embodiment, a bronchoscope 134 is used as the delivery device 132, and the bronchoscope 134 has a construction in which the embolization element 131 is attached to its leading end portion or a construction which holds the embolization element 131 by means of an insertion assistance device capable of being introduced into the leading end portion through a channel of the bronchoscope 134.

The operation of the eighth embodiment having the above-described construction will be described below. When the bronchus embolization device 101 of the eighth embodiment is to be used, the bronchoscope 134 is inserted into the bronchus H4 of the patient H. Subsequently, a leading end portion of the insertion assistance device is inserted into the internal cavity of the bronchus H4 which is an embolization target, via the channel of the bronchoscope 134, thereby placing the embolization element 131.

At this time, the operator observes the surface of the lung H2 through the optical viewing tube 104 of the observation device 102 inserted into the pleural cavity H1, and confirms that the lung-emphysema-affected portion H5 does not inflate with respiration during the embolization of the bronchus H4. Thus, the operator can determine whether the bronchus H4 distributed in the lung-emphysema-affected portion H5 is reliably embolized.

In addition, to confirm the embolized part of the bronchus H4, it is also possible to use a balloon catheter or the like. For example, in the case where the bronchoscope 134 is used as a treatment device, it is possible to temporarily embolize the internal cavity of the bronchus H4 which is an embolization target, by inserting the balloon catheter from the channel of the bronchoscope 134 and inflating the balloon of the balloon catheter.

Furthermore, the operator practices artificial respiration with the bronchus H4 which is an embolization target, and observes the surface of the lung H2 through the optical viewing tube 104 in the pleural cavity H1, whereby the operator can confirm which part is embolized, because a lung tissue in which the embolized bronchus H4 is distributed does not inflate with respiration. Accordingly, the operator can search for a position in which the lung-emphysema-affected portion H5 does not inflate, and repeatedly perform temporary embolization of the bronchus internal cavity H6, and therefore, can place the embolization element 131 after having confirmed the target part.

Furthermore, after the balloon catheter has been introduced to the bronchus H4 which is an embolization target, if the balloon is inflated to temporarily embolize the bronchus H4 and a positive pressure is applied to the interior of the bronchus H4 from the channel of the balloon catheter, the operator can confirm the embolized part by means of the observation device 102 in the pleural cavity H1, whereby the operator can confirm highly accurately a part which is high in emphysematous change (embolization area).

Accordingly, the eighth embodiment having the above-described construction serves the following advantages. Namely, the bronchus embolization device 101 of the eighth embodiment includes, instead of the treatment device 103 to be inserted into the pleural cavity H1 through the trocar 113 made to puncture the chest wall H21 as in the seventh embodiment, the embolization element placing device 133 which is made of the embolization element 131 to be placed in the bronchus H4 to completely embolize the bronchus internal cavity H6, and the delivery device 132 to be inserted into the bronchus H4 to guide the embolization element 131 to a placement position. Accordingly, it is possible to give treatment to lung emphysema with a small invasion. Furthermore, the eighth embodiment also has the advantage that since invasions into the lung tissue and the bronchus tissue of the patient H are small, the patient H can recover quickly after the surgical operation.

Figure 22:
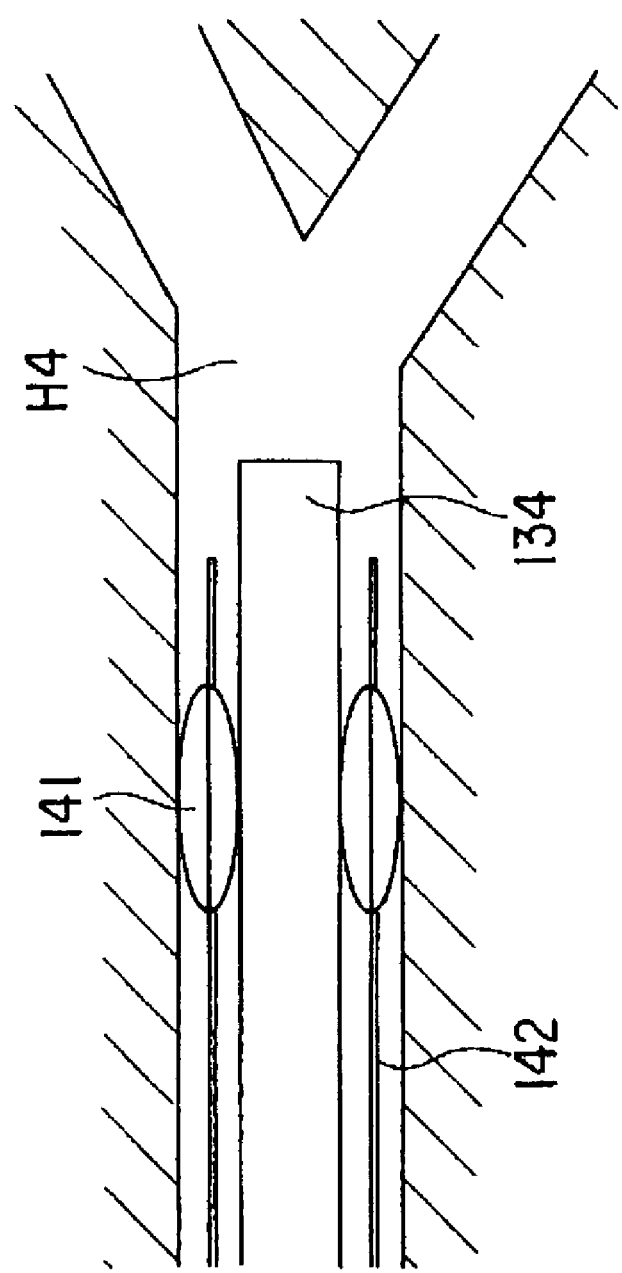
FIG. 22 is a longitudinal sectional view of the portions showing a modification of the bronchus embolization device of the eighth embodiment.

FIG. 22 shows a modification of the bronchus embolization device 101 of the eighth embodiment (refer to FIG. 21). This modification has a construction in which an overtube 142 having a cuff 141 is fitted on the peripheral surface of a leading portion of the bronchoscope 134 or in which a cuff is provided at the leading portion of the bronchoscope 134. In either construction, similar advantages can be expected.

In this case, since the embolization element 131 can be guided to the target bronchus H4 by the above-described method, it is possible to quickly embolize the bronchus H4 after the air stored in the lung-emphysema-affected portion H5 to be embolized has been removed by sucking the interior of the bronchus H4 through the channel of the bronchoscope 134 with the cuff 141 expanded. According to this method, not only does the effect of treatment appear quickly, but since the pressure inside the bronchus on the peripheral side of the embolized part becomes small, there is the advantage that it is possible to avoid the risk that the placed embolization element 131 moves to a bronchus (having a larger inside diameter) lying on the central side of the embolized part.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

The invention claimed is:

1. A method of embolizing a bronchus/bronchiole of a subject, comprising:
   guiding a puncture portion of an injection device to a part to be embolized in the bronchus/bronchiole of the subject;
   puncturing a mucosa of the bronchus/bronchiole in the part to be embolized with the puncture portion of the injection device; and
   injecting an injection material into a submucosa of the bronchus/bronchiole to swell an inside wall of the bronchus/bronchiole.

2. The method of embolizing a bronchus/bronchiole according to claim 1, wherein the injection device includes a catheter having, at its leading end, a puncture portion capable of puncturing a mucosa of the bronchus/bronchiole and, at its distal end, a connection portion to which to connect a syringe, the injection material being injected by the syringe.

3. The method of embolizing a bronchus/bronchiole according to claim 1, wherein the injection material contains a fibrin adhesive or collagen.

4. The method of embolizing a bronchus/bronchiole according to claim 1, wherein the injection material is a material in which a particulate substance which is a solid component is suspended in a liquid base material.

5. The method of embolizing a bronchus/bronchiole according to claim 4, wherein the particulate substance is selected from a group consisting of silicone, metal particles, apatite and β-TCP.

6. The method of embolizing a bronchus/bronchiole according to claim 1, further comprising adding a curing agent to the injected injection material after the injecting of the injection material into the submucosa of the bronchus/bronchiole.

7. The method of embolizing a bronchus/bronchiole according to claim 1, wherein the injection material has a property to expand by absorbing water in a living body.

8. The method of embolizing a bronchus/bronchiole according to claim 2, wherein:
   the injection device further includes an endoscope having a channel through which to insert the catheter, and a cap capable of being attached to a leading end of the endoscope, a cap having a sheath which guides a puncture portion of the catheter from a leading opening of the channel to a through-hole opened in the cap,
   the method further comprising guiding the puncture portion from the opening of the channel to the through-hole.

9. The method of embolizing a bronchus/bronchiole according to claim 8, wherein:
   a balloon is attached to the side opposite to the side in which the through-hole is opened,
   the method further comprising expanding the balloon after guiding the puncture portion of the injection device to the part to be embolized.

* * * * *